United States Patent [19]
Dhority et al.

[11] Patent Number: 5,236,088
[45] Date of Patent: Aug. 17, 1993

[54] BIOMEDICAL MATERIAL SHIPMENT KIT AND METHOD

[75] Inventors: Mitchell A. Dhority, Southaven, Miss.; Denice C. Pian, Germantown; Paul J. Wisnewski, Memphis, both of Tenn.

[73] Assignee: Smith & Nephew Richards, Inc., Memphis, Tenn.

[21] Appl. No.: 922,028

[22] Filed: Jul. 29, 1992

[51] Int. Cl.⁵ .................. B65D 81/24; B65D 81/26; B65D 81/02; A61J 1/00

[52] U.S. Cl. .................. 206/438; 215/367; 206/459.5; 206/524.4; 206/523; 206/526; 206/205; 422/1

[58] Field of Search .................. 215/365-367; 206/438, 459.5, 524.4, 523, 526, 205; 422/1

[56] References Cited

U.S. PATENT DOCUMENTS

| | | |
|---|---|---|
| 3,236,206 | 2/1966 | Willinger . |
| 3,255,871 | 6/1966 | Butler . |
| 3,810,367 | 5/1974 | Peterson . |
| 4,011,947 | 3/1977 | Sawyer . |
| 4,368,819 | 1/1983 | Durham . |
| 4,470,264 | 9/1984 | Morris . |
| 4,474,016 | 10/1984 | Winchell . |
| 4,530,816 | 6/1985 | Douglas-Hamilton . |
| 4,723,974 | 2/1988 | Ammerman . |
| 4,750,619 | 6/1988 | Cohen et al. . |
| 4,766,740 | 8/1988 | Bradley et al. . |
| 4,872,553 | 10/1989 | Suzuki et al. . |
| 4,913,700 | 4/1990 | Kantrowitz et al. ............ 206/438 |
| 4,947,658 | 8/1990 | Wheeler et al. . |
| 4,955,480 | 9/1990 | Sexton . |
| 4,958,506 | 9/1990 | Guilhem et al. . |
| 5,040,678 | 8/1991 | Lenmark, Sr. et al. . |

FOREIGN PATENT DOCUMENTS 336107 10/1989 European Pat. Off. ............ 206/438

OTHER PUBLICATIONS

Federal Register, vol. 57, No. 53, Wed., Mar. 18, 1992, pp. 9402-9404, Postal Service Proposed Rule for Inclusion in 39 CFR Part 111, Mailability of Sharps and Other Medical Devices.

EnduroTherm TM Marketing Brochure, distributed by Insulated Shipping Containers, Inc. (ISC) Apr. 1991.

*Primary Examiner*—William I. Price
*Attorney, Agent, or Firm*—Pravel, Hewitt, Kimball & Krieger

[57] ABSTRACT

An orthopedic implant retrieval kit which, when assembled, provides a shipping and handling container for explanted orthopedic devices which will protect individuals handling the container from the material in the container, and which will meet the appropriate regulations for shipping of potentially biohazardous material. The kit includes at least three plastic bags, at least two containers, a box, at least one foam insert, instructions and labels. The method involves assembling the kit components into a container for shipment.

12 Claims, 4 Drawing Sheets

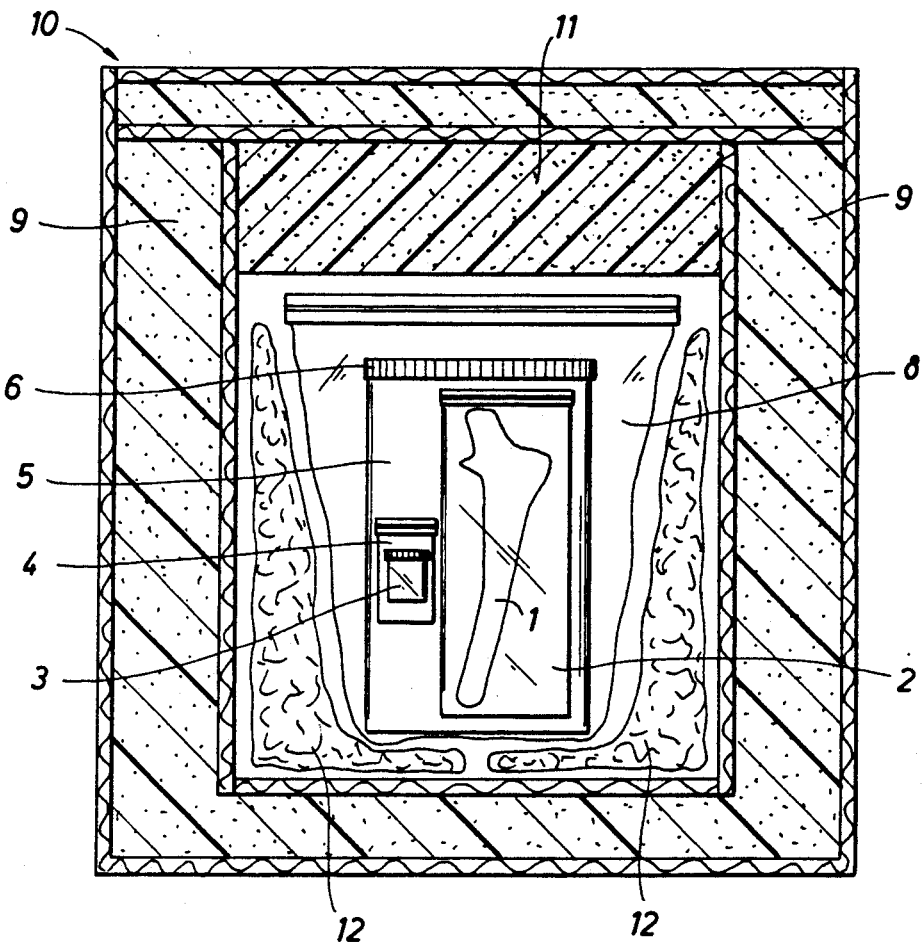
FIG. 1
PATIENT _____
DEVICE NAME _____
QC NUMBER _____
SURGEON _____
REVISION DATE _____
FIG. 4A
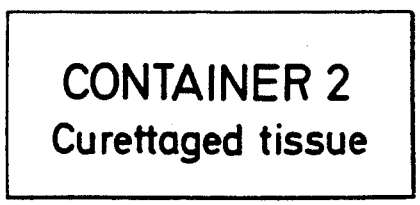
FIG. 4B

PACKING INSTRUCTIONS

1. Complete label (Label 1) on the provided specimen container (Container 1) with patient name, device name, QC number, surgeon and revision date.
2. Complete label (Label 2) on interior of shipping box with surgeon name, patient name, and retrieval date.
3. Place device into provided zip lock bag (Bag 1).
4. ADD 10% FORMALIN TO ZIP LOCK BAG WITH DEVICE UNTIL HALF FULL AND CLOSE BAG.
5. Place zip lock bag with device into specimen container (Container 1)
6. Place curettaged tissue (if applicable) into specimen container (Container 2) with 10% formalin and close container.
7. Place container 2 into zip lock bag (Bag 2) and close.
8. Place zip lock bag with container of corettaged tissue into container 1.
9. Close lid of container 1 and tape lid with heavy tape.
10. Place entire container into provided outer zip lock bag (Bag 3) and seal.
11. Place absorbent material (news print, standard paper towels, etc.) into box bottom.
12. Place zip lock bag (Bag 3) with specimen container(s) (Container 1) into shipping box.
13. Place foam insert into top of box.
14. Close and seal box with strong tape.
15. Affix enclosed black and white striped Class 9 label (Label 3) to outside of box.
16. Affix enclosed Formaldehyde Solution label (Label 4) to outside of box.
17. Affix enclosed shipping label (Label 5) to outside of box.
18. Complete the following sections of the enclosed Federal Express airbill :
    A. Sender information (at top left)
    B. Airport of departure (five lines up from bottom)
    C. Name and title of shipper, place and date, emergency telephone, and signature (bottom of airbill).

FIG.3

| TOTAL JOINT RETRIEVAL KIT |
|---|
| SURGEON : _____ |
| PATIENT : _____ |
| DATE OF REVISION SURGERY : _____ |

WARNING
POSSIBLE BIOHAZARD
Contains
Retrieved human implant
preserved in formalin Handle opened container
with gloved hands If damaged during shipping, isolate container and
contact :

FORMALDEHYDE
SOLUTIONS
UN 2209

BIOMEDICAL MATERIAL SHIPMENT KIT AND METHOD

BACKGROUND OF THE INVENTION

1. Field of the Invention

This invention relates to a kit for assembly of a container which is suited for the handling and shipping of explanted orthopedic implants and/or tissue samples or other potentially biohazardous materials.

2. Description of the Related Art

When orthopedic implants are removed from patients ("explanted orthopedic devices"), they must frequently be shipped to the manufacturer, often with an accompanying tissue sample, for examination and/or analysis for a variety of reasons, including regulatory responses. These materials are potentially biohazardous to those individuals handling the items during retrieval, shipping and examination.

In the past, medical personnel responsible for returning explanted orthopedic devices had to package, label, and ship the items by using packaging and labels chosen at their own discretion, which were often less than adequate. Many packages were packed and labeled in a manner lacking protection for those handling the package from potentially contaminated material.

Regulations have been promulgated by various agencies and associations relating to the shipping, handling, and mailing of such biomedical materials. The Postal Service proposed a rule for inclusion in 39 Code of Federal Regulations (CFR) Part 111, Mailability of Sharps and Other Medical Devices (Federal Register, Vol. 57, No. 53, Wed., Mar. 18, 1992), which states in part:

... used medical devices which do not have or contain a projecting sharp [sic] must be packaged in a securely sealed, leak resistant primary container. The primary container must be enclosed in a shipping container that is constructed of 275-pound grade corrugated fiberboard or similar material of equivalent strength. The total volume of liquid in the primary and shipping container must not exceed 50 ml., unless the devices are mailed in a formalin solution or its equivalent. There must be sufficient absorbent material between the primary and shipping container to absorb three times the total liquid allowed within the primary container, except when the device is being shipped in a formalin solution.

Several patents describe methods and devices for preserving and transporting biological materials or prosthetic devices. U.S. Pat. No. 3,255,871 to Butler is directed to the use of a translucent plastic bag in which a formaldehyde solution is formed in situ for preserving and transporting biological material. For long distance transportation, the bag is placed in a suitable shipping carton. However, this product does not afford the protection provided by multiple liquid sealed barriers so that any leakage from this primary container could potentially infect handlers thereof.

U.S. Pat. No. 4,011,947 to Sawyer describes a packaged prosthetic device and a packaging technique designed so that a prosthetic device will arrive at its ultimate position for installation in a sterile and clean condition. However, this patent does not describe a method or device for handling and shipping a potentially biohazardous material, partially those shipped in a liquid preservative.

U.S. Pat. No. 4,530,816 to Douglas-Hamilton describes a method and device for cooling, preserving and transporting biological material such as equine semen specimens and equine embryos, with the primary concern being to maintain a specified temperature range for increased viability.

Thus, there is a need to provide a kit so that a shipping container can be assembled for a variety of explanted orthopedic devices and/or tissue samples and other biomedical materials, such that these items can be handled and shipped in a safe and non-degenerative manner. This need is particularly apparent in view of the current AIDS epidemic and the known transmittal of the AIDS virus through bodily fluids.

SUMMARY OF THE INVENTION

The present invention is directed to a kit for assembling a container for explanted orthopedic devices and tissue samples, which has several internal barriers against leakage to provide protection to an individual handling the container against possible exposure to potentially contaminated fluids.

The kit includes three transparent, fluid impermeable plastic bags of different sizes, two transparent, fluid impermeable rigid containers of different sizes, a box, and foam inserts, all of which are designed for assembly into a shipping and handling container for explanted orthopedic devices and/or tissue samples or other biomedical materials. The invention additionally provides, as components in the kit, detailed packing instructions and appropriate shipping labels and forms. The box is formed of inner and outer corrugated cardboard with a layer of polyurethane foam in the middle.

The invention also involves a method of packing and shipping an explanted orthopedic device and/or a tissue sample in a liquid preservative, such that these potentially biohazardous materials can be shipped in a manner which is safe to the individuals handling the package. After an orthopedic implant is removed from a patient, it is placed in a plastic bag, which has a slidable seal, such as the commonly known ZIPLOC® bag. A formalin solution or other preservative is added and the bag is sealed. A tissue sample from the site of the implant may be obtained and placed in one of the containers, a formalin solution is added and the container is then sealed. The container is placed in a second plastic bag and sealed. Both plastic bags are placed in a second solid container, which is then sealed. That container is placed in a third plastic bag which is then sealed and placed in the box and made ready for shipping by surrounding the third plastic bag with added absorbent material (i.e., paper towels or the like), and a foam insert to prevent any undue movement or leakage inside the box.

The kit also includes detailed packing instructions and labels/forms to be attached to the various components of the kit.

BRIEF DESCRIPTION OF THE DRAWINGS

The invention can be better understood by referring to the detailed description of an exemplary embodiment set forth below, in conjunction with the appended drawings, in which:

FIG. 1 is a sectional view of a box containing the assembled components of an orthopedic implant retrieval kit;

FIG. 3 is an example of a packing instruction sheet;

FIGS. 4A and 4B are examples of a specimen container label;

DETAILED DESCRIPTION OF AN EXEMPLARY EMBODIMENT

Figures 2, 5:
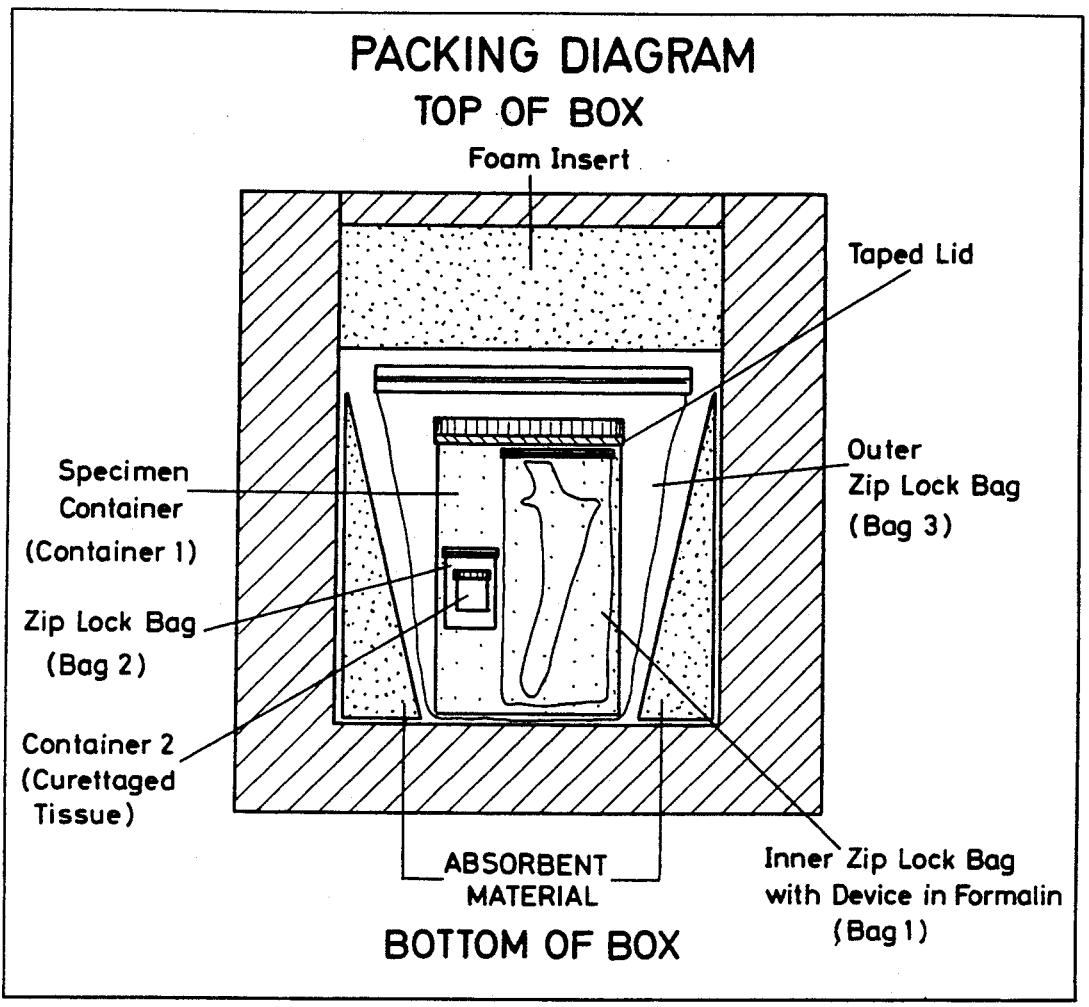
FIG. 2 is an example of a packing diagram for the kit of FIG. 1.
FIG. 5 is an example of an inner box label.

FIG. 1 shows components of an orthopedic implant retrieval kit used for packing an explanted orthopedic device and/or tissue sample or other biomedical material. As shown, the components of the kit have been utilized in packing an orthopedic device and/or related tissue sample into a shipping container 10. The components of the kit are described below in conjunction with an exemplary method for packing such materials.

An explanted orthopedic device 1 is placed in a first plastic bag 2. A suitable amount of 10% formalin solution (formaldehyde) is added, preferably filling the bag 2 approximately half full. The bag 2 is then closed and sealed. The bag 2 is formed in a size and shape suitable for holding the explanted orthopedic device 1 and formaldehyde and providing a liquid seal. Preferably, the bag 2 is a 1-gallon, transparent, resealable and fluid impermeable, with a zipper close top, of the type currently used for freezer storage. The bag 2 may be a ZIPLOC® heavy duty freezer bag manufactured by DowBrands, Inc. of Indianapolis, Ind.

A tissue sample (not shown) which may be removed from the same site as the orthopedic device 1, is placed in a first transparent container 3. A 10% formalin solution (formaldehyde) is added to a suitable level, and the container 3 is closed and sealed. The container 3 is formed in a size and shape suitable for holding the tissue sample and formaldehyde and providing a liquid seal. Preferably, the container 3 is a rigid or semi-rigid, screw cap, specimen container of the type commonly used in the medical industry. The container 3 can be a screw cap specimen container as manufactured by Becton Dickinson Labware of Lincoln Park, N.J.

The container 3 is placed in the second transparent plastic bag 4 which is of a size and shape suitable for holding the container 3 and providing a liquid seal. Preferably, the bag 4 may be a 1-quart size ZIPLOC® heavy duty freezer bag.

Both bags 2, 4 are placed in a second container 5, which is then closed and sealed. The second container has a lid 6 that may further be sealed with heavy tape (not shown). The second container 5 is sized and shaped to hold both the bag 2 and the bag 4 and provide a liquid seal. Preferably, the second container 5 is an 83 oz., rigid HDPE multipurpose container with a "snap tight" top, manufactured by VWR Scientific Co. of Bridgeport, N.J. Other containers formed of a rigid or semirigid plastic may also be used.

The container 5 is placed in a third plastic bag 8 which is closed and sealed. Preferably, the third plastic bag 8 is a 13 in. × 18 in., 4 mil. plastic bag with a zipper-type closure that is produced by Consolidated Plastics Company, Inc. of Twinsburg, Ohio.

The bag 8 is placed in a box 9, which may be an EnduroTherm ™ insulated container, produced by Insulated Shipping Containers of Phoenix, Az., that is formed by injecting a polyurethane foam between two layers of corrugated cardboard within a mold, which produces a rigid, one-piece, three-layer laminated box. Pieces of absorbent material 12, such as absorbent pads or wadded-up paper towels, are added around and under the bag 8 to prevent undue leakage into the walls of the box 9. A foam insert 11 is packed between the bag 8 and the inner wall of the box 9 to cushion and support the bag 8. The box 9 is then closed, sealed and prepared for shipping.

Detailed packing instructions, shipping labels and forms are included in the kit and shown in FIGS. 2–8. An example of a set of packing instructions is set forth below (note that reference numerals in the packing instructions refer to items in the kit as shown on the packing diagram instruction sheet of FIG. 2, not to reference numbers in FIG. 1):

PACKING INSTRUCTIONS

1. Complete label (Label 1) on provided specimen container (Container i) with patient name, device name, QC number, surgeon, and revision date.
2. Complete label (Label 2) on interior of shipping box with surgeon name, patient name, and retrieval date.
3. Place device into provided zip lock bag (Bag 1).
4. Add 10% formalin to zip lock bag with device until half-full and close bag.
5. Place zip lock bag with device into specimen container (Container 1).
6. Place curettaged tissue (if applicable) into specimen container (Container 2) with 10% formalin and close container.
7. Place container 2 into zip lock bag (Bag 2) and close.
8. Place zip lock bag with container of curettaged tissue into container 1.
9. Close lid of container 1 and tape lid with heavy tape.
10. Place entire container into provided outer zip lock bag (Bag 3) and seal.
11. Place absorbent material (news print, standard paper towels, etc.) into box bottom.
12. Place zip lock bag (Bag 3) with specimen container(s) (Container 1) into shipping box.
13. Place foam insert into top of box.
14. Close and seal box with tape.
15. Affix enclosed black and white striped Class 9 label (Label 3) to outside of box.
16. Affix enclosed formaldehyde solution label (Label to outside of box.
17. Affix enclosed shipping label (Label 5) to outside of box.
18. Complete the following sections of the enclosed Federal Express airbill:
    A. Sender information (at top left);
    B. Airport of departure (5 lines up from bottom);
    C. Name of title of shipper, place and date, emergency telephone, and signature (bottom of airbill).

Shipping labels and forms mentioned in the packing instructions are described below:

1) Packing Diagram and Instruction Sheet (FIGS. 2 and 3)—these labels are placed on the inside of a top flap (not shown) of the box 9 prior to shipment to the customer and illustrate the proper assembly of the various components of the kit.
2) Specimen Container Labels (FIGS. 4A and 4B)—the label of FIG. 4A is placed on the second container 5 prior to shipment to the customer and is to be completed by the customer. It identifies relevant information about the orthopedic device, the surgery, and the surgeon. The label of FIG. 4B is placed on the container 3 prior to shipment to the customer and identifies the contents.

3) Inner Box Label (FIG. 5)—this label is placed on the inside of a top flap (not shown) of the box 9 prior to shipment to the customer and identifies the surgeon, patient and date of surgery.

Figure 6A:
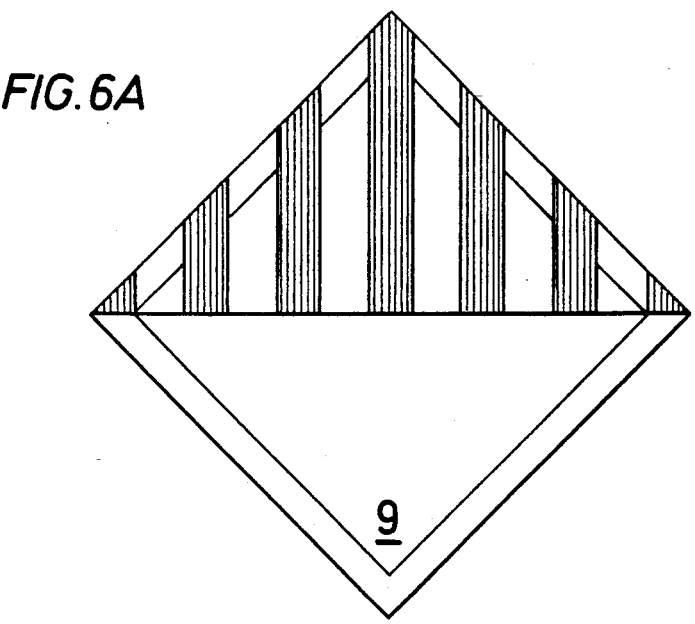
FIGS. 6A and 6B are examples of dangerous goods warning labels.
Figure 6B:
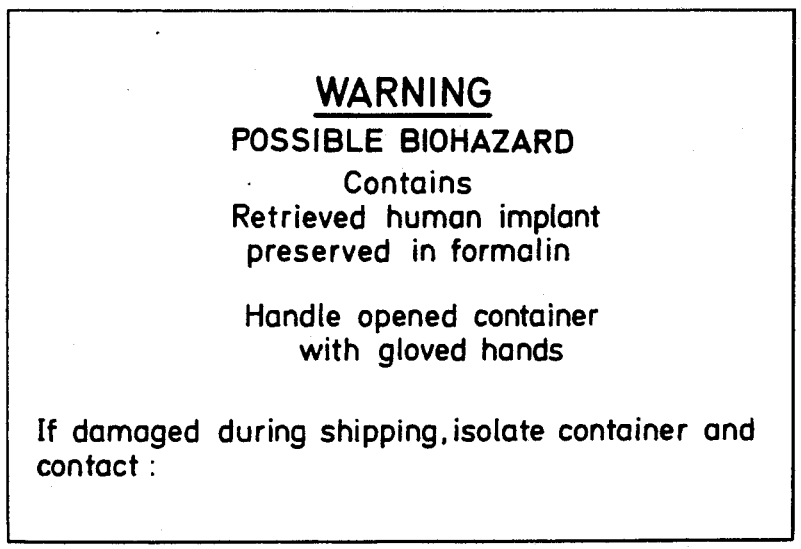
Figure 7:
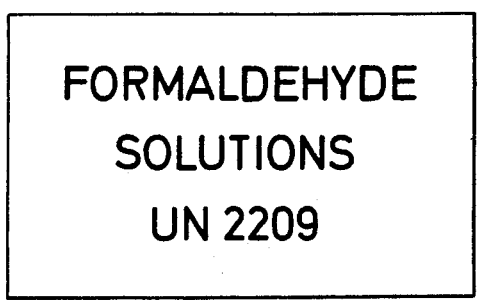
FIG. 7 is an example of a formaldehyde solutions label.
Figure 8:
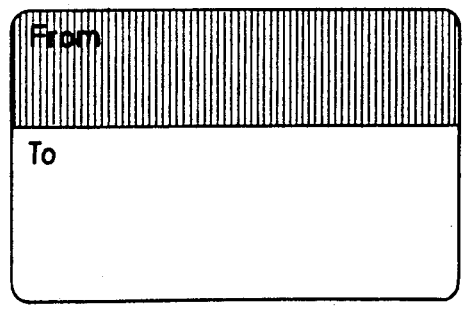
FIG. 8 is an example of a return label.

4) Dangerous Goods Warning Labels (FIGS. 6A and 6B)—these labels identify the specific class in which the dangerous good is categorized, as required by both the U.S. Dept. of Transportation (DOT) and International Air Transport Association (IATA) regulations. The label of FIG. 6A is supplied to the customer to be affixed to outer surface of the box 9 at the time the explanted orthopedic device 1 is packaged and shipped. The label of FIG. 6B is preattached to the container 5 in order to identify the contents in the event of inadvertent damage to the package during shipping.

5) Formaldehyde Solution Warning Label (FIG. 7) —this label warns the freight carrier that the box 9 contains a dangerous good (formaldehyde solution), as required by both DOT and IATA regulations. The label is supplied to the customer to be affixed to the outer surface of the box 9 at the time the explanted orthopedic device I is packaged and shipped.

6) Shipping Label (FIG. 8)—this label identifies both the shipper and recipient in the event that the freight carrier needs to contact either one, as required by both DOT and IATA regulations. The label is supplied to the customer to be affixed to the shipping container 10 at the time the explanted orthopedic device 1 is packaged and shipped.

7) Overnight Delivery Airbill Form (not shown), where appropriate.

The kit, with all component parts described above, is sent in an unlabeled box 9 to the party who wants to ship an explanted orthopedic device. The kit includes all materials that are necessary for labeling, packing and shipping the explanted orthopedic device 1. The components are labeled to correspond with the packing instructions.

The kit solves the problems mentioned above by providing in one package all the elements required by appropriate regulations for shipping potentially hazardous biomedical material. The sender only needs to package the material and send it. The need to search for any of the necessary packing materials and the possibility of the packer using non-approved packing materials, are thereby eliminated.

Having described the invention above, various modifications of the techniques, procedures, material and equipment will be apparent to those skilled in the art. It is intended that all such variations within the scope and spirit of the invention be included within the scope of the appended claims.

What is claimed is:

1. A kit for the safe handling and shipping of biomedical materials in a liquid preservative, comprising:
   (1) a first generally flexible sealable container for holding an explanted orthopedic device and a liquid preservative and for providing a liquid sealed barrier, said first generally flexible container being sized and shaped to permit the introduction of the explanted orthopedic device therein;
   (2) a first generally rigid sealable container for holding a tissue sample and a liquid preservative and for providing a liquid sealed barrier, said first generally rigid container being sized and shaped to permit the introduction of the tissue sample therein;
   (3) a second generally flexible sealable container for holding the first generally rigid container and for providing a liquid sealed barrier, said second generally flexible container being sized and shaped to permit the introduction of the first generally rigid container therein;
   (4) a second generally rigid sealable container for holding both the first and second generally flexible containers and for providing a liquid sealed barrier, said second generally rigid container being sized and shaped to permit the introduction of both the first and second generally flexible containers therein;
   (5) a third generally flexible sealable container for holding the second generally rigid container and for providing a liquid sealed barrier, said third generally flexible container being sized and shaped to permit the introduction of the second generally rigid container therein;
   (6) a box for containing the third generally flexible container, said box being sized and shaped to hold the third generally flexible container therein;
   (7) at least one foam insert for placement in the box for supporting and cushioning the third bag within the box; and
   (8) instructions and labels for the proper assembling and shipping of the components of the kit.

2. The orthopedic implant retrieval kit of claim 1, wherein the box is formed of a three layer laminate material having polyurethane foam sandwiched between two layers of corrugated cardboard.

3. The orthopedic implant retrieval kit of claim 1, wherein the first, second, and third generally flexible containers are formed of a transparent, flexible plastic material.

4. The orthopedic implant retrieval kit of claim 1, wherein the first, second, and third generally flexible containers include a zipper close top.

5. The orthopedic implant retrieval kit of claim 1, wherein the first and second generally rigid containers are formed of a transparent plastic material.

6. The orthopedic implant retrieval kit of claim 1, wherein the first and second generally rigid containers are formed of a semi-rigid material.

7. The orthopedic implant retrieval kit of claim 1, wherein the first and second generally rigid containers are formed of a rigid material.

8. The orthopedic implant retrieval kit of claim 1, wherein the first and second generally rigid containers have snap-on caps.

9. The orthopedic implant retrieval kit of claim 1, wherein the labels comprise:
   at least one label for identification of the explanted orthopedic device;
   at least one packing diagram label to aid in kit assembly; and
   at least one identification label which complies with appropriate regulations.

10. A method of packing and shipping an explanted orthopedic device and a tissue sample in a liquid preservative comprising the steps of:
   (a) selecting an orthopedic implant retrieval kit having the components set forth in claim 1;

(b) placing the explanted orthopedic device in the first generally flexible container;
(c) adding a liquid preservative to the first generally flexible container;
(d) sealing the first generally flexible container;
(e) sealing the first generally flexible container within the second generally rigid container;
(f) sealing the second generally rigid container within the third generally flexible container;
(g) placing the third generally flexible container within the box; and
(h) placing absorbent material around at least a portion of the third generally flexible container;

(i) supporting and cushioning the third bag within the box with at least one form insert.

11. The method of claim 10, further comprising the steps of:
(a) placing a tissue sample in the first generally rigid container;
(b) adding a liquid preservative to the first generally rigid container;
(c) sealing the first generally rigid container;
(d) sealing the first generally rigid container within the second generally rigid container along with the first generally flexible container.

12. The method of claim 10, further comprising the step of shipping the assembled kit.

* * * * *